United States Patent [19]

Jensen et al.

[11] 4,338,334
[45] Jul. 6, 1982

[54] 1-[4-(4-SULFANILYL)PHENYL] UREA AND DERIVATIVES IN COMPOSITIONS AND METHODS OF TREATING RHEUMATOID ARTHRITIS AND IMMUNE COMPLEX DISEASES

[75] Inventors: Norman P. Jensen, New Providence; David P. Jacobus, Princeton; Howard Jones, Holmdel, all of N.J.

[73] Assignee: Merck & Co., Inc., Rahway, N.J.

[21] Appl. No.: 126,045

[22] Filed: Feb. 29, 1980

Related U.S. Application Data

[63] Continuation-in-part of Ser. No. 865,560, Dec. 29, 1977, abandoned.

[51] Int. Cl.$^3$ .................. A61K 31/16; A61K 31/17; A61K 31/275; A61K 31/655
[52] U.S. Cl. ........................... 424/322; 424/226; 424/273 R; 424/282; 424/283; 424/304; 424/311; 424/320; 424/324
[58] Field of Search ............... 424/322, 226, 304, 311, 424/320, 324

[56] References Cited

U.S. PATENT DOCUMENTS

| | | | |
|---|---|---|---|
| 3,165,510 | 11/1965 | Hoenen et al. | 424/322 |
| 3,689,671 | 9/1972 | Johnston et al. | 424/322 |
| 3,702,362 | 11/1972 | Shen et al. | 424/322 |
| 3,715,375 | 2/1973 | Shen et al. | 260/397.6 |
| 3,717,623 | 2/1973 | Ruyle | 424/322 |
| 3,775,403 | 11/1973 | Shen et al. | 260/239.8 |
| 3,775,444 | 11/1973 | Jenson et al. | 260/397.6 |
| 3,786,050 | 1/1974 | Shen et al. | 260/239.6 |

FOREIGN PATENT DOCUMENTS 2203626 10/1972 France ........................... 424/322

OTHER PUBLICATIONS

McConkey et al., Rheumatology and Rehabilitation, 1976, 15, 230–234.
Northey, "Sulfonamides", A.C.S. Monograph, pp., 340–376, No. 106, (1948).
Gemmell et al., Br. J. Pharmacol, 61, 92–93, (1977).
Shigeura et al., Biochemical Pharmacology, vol. 24, pp. 687–691, (1975).
J. Sci. Ind. R., 34(a) 521–526,(1975).

Primary Examiner—Allen J. Robinson
Attorney, Agent, or Firm—Theresa Y. Cheng; Raymond M. Speer; Mario A. Monaco

[57] ABSTRACT

The invention relates to 1-[4-(4-sulfanilyl)phenyl] urea and derivatives thereof in pharmaceutical compositions and in methods of treating rheumatoid arthritis and immune complex diseases such as dermatitis herpetiformis.

6 Claims, No Drawings

1-[4-(4-SULFANILYL)PHENYL] UREA AND DERIVATIVES IN COMPOSITIONS AND METHODS OF TREATING RHEUMATOID ARTHRITIS AND IMMUNE COMPLEX DISEASES

REFERENCE TO RELATED APPLICATIONS

This application is a continuation-in-part of application Ser. No. 865,560, filed Dec. 29, 1977, now abandoned.

BACKGROUND OF THE INVENTION

1. Field of the Invention

The present invention is concerned with pharmaceutical compositions containing as an active ingredient the known compound 1-[4-(4-sulfanilyl)phenyl]urea and known derivatives thereof, and the use of these compositions, or the compounds themselves, in treating rheumatoid arthritis, muscular dystrophy, immune complex diseases, including dermatitis herpetiformis, celiac disease, and certain forms of leukemia, and autoimmune endocrine diseases such as juvenile diabetes.

2. Description of the Prior Art

Dapsone (4,4'-diaminodiphenylsulfone) is an established antimalarial and antileprotic agent. It has been found to be effective in treating rheumatoid arthritis; see McConkey et al., *Rheumatology and Rehabilitation*, 1976, 15, 230–234. It has also been employed in clinical treatment of dermatitis herpetiformis; see Lorincz and Pearson, "Sulfapyridine and Sulfone Type Drugs in Dermatology", *Arch. Derm.* 85: 42–56 (1962). Derivatives of diaminodiphenyl sulfone have been described in the literature for many years; see E. H. Northey, "Sulfonamides", A.C.S. monograph No. 106 (1948). The compound 1-[4-(4-sulfanilyl)phenyl]urea, as well as a variety of substituted diphenyl sulfones have been found useful in reducing mortality and decreasing lesion incidence of poultry exposed to Marek's disease. See U.S. Pat. Nos. 3,689,671; 3,702,362; 3,715,375; 3,775,403; 3,775,444; and 3,786,050. However, none of these patents suggests the use of the substituted diphenyl sulfones disclosed therein as agents for treating rheumatoid arthritis, muscular dystrophy, or immune complex diseases.

The compound 1-[4-(4-sulfanilyl)phenyl]urea, and several substituted diphenyl sulfones have been found to inhibit the incorporation of chloline in chick peritoneal macrophages, an activity associated with the ability of such compounds to suppress growth or function of Marek's disease virus. See Shigeura et al., "Metabolic Studies on Diphenylsulfone Derivatives in Chick Macrophages", *Biochemical Pharmacology*, Vol. 24, pp. 687–691 (1975).

SUMMARY OF THE INVENTION

The present invention is concerned with a method of treating rheumatoid arthritis, muscular dystrophy, and certain immune complex diseases, particularly dermatitis herpetiformis.

Rheumatoid arthritis is a debilitating disorder of the joints marked by inflammation and degeneration of the connective tissue of the joints. And it is generally believed that part of the pathogenic sequence of rheumatoid arthritis is caused by or through immune complexes. However, rheumatoid arthritis remains a poorly understood disease, and in spite of the extensive research which has been carried out over the past two decades in search of effective and well tolerated agents for the treatment of rheumatoid arthritis, few such agents have been discovered, and a need still exists for new drugs in this area. While conventional non-steroidal, anti-inflammatory-analgesic-antipyretic agents, such as aspirin, are effective in providing symptomatic relief of the acute syndrome characterizing rheumatoid arthritis, they are unable to alter the course of the disease. As a consequence, the anti-rheumatic actions of two old remedies, gold and D-penicillamine, in spite of their potential side effects, have received renewed interest in the past few years. It is now well documented that these two agents can alter the course of the disease both pathologically and in reducing the immune complexes as measured by rheumatoid factor titers. It is thus significant that dapsone has the same clinical effect.

Dermatitis herpetiformis is a relatively rare immune complex disease of unknown etiology. The characteristic lesions are reported to be due to the deposition of the immune complexes. Also, patients with this disease carry an increased incidence of the Human Leukocyte Antigen HLA-B8, which is linked with HLA-DW3. Autoimmune patients carrying these surface lymphocyte markers have an enhanced susceptibility to dermatitis herpetiformis and also have an enhanced susceptibility to certain other diseases sharing these same lymphocyte markers. Examples of these other diseases, are celiac disease, certain forms of leukemia, and autoimmune endocrine diseases such as juvenile diabetes. Lymphocyte transformation and proliferation in response to foreign antigens has been known to be a component common to many of the pathological processes which characterize autoimmune and immune complex mediated diseases. It is, therefore, significant that dapsone and 1-[4-(4-sulfanilyl)phenyl]urea effect lymphocyte transformation.

Macrophage migration and activation are a component part of the continuing pathological processes in joint destruction. It is also, therefore, significant that dapsone and 1-[4-(4-sulfanilyl)phenyl]urea both inhibit the incorporation of the natural constituent of cell-membranes, choline, into the mammalian macrophage membrane; an indication that the ability of this phagocytic cell to respond to exogenous inflammatory stimuli is inhibited by the subject compounds.

Furthermore, one of the major deleterious side effects of dapsone therapy, termed the "dapsone effect" (*J. Sci. Ind. R.*, 34 (9), 521–526, 1975) is severe progressive anemia measured by a sharp increase in methemoglobin. When a laboratory assay for methemoglobin formation was performed in mice 1-[4-(4-sulfanilyl)phenyl]urea and derivatives were significantly less active in producing this toxic syndrome. 1-[4-(4-sulfanilyl)phenyl]urea and derivatives are also less acutely toxic than dapsone as measured by $LD_{50}$'s in mice.

Accordingly, 1-[4-(4-sulfanilyl)phenyl]urea and derivatives have utility in the treatment of rheumatoid arthritis and immune complex or autoimmune diseases linked to an increased incidence of human leukocyte antigen markers, with significantly less side-effects than dapsone.

The 1-[4-(4-sulfanilyl)phenyl]urea and derivatives thereof useful in pharmaceutical compositions and in methods of treating rheumatoid arthritis muscular dystrophy, and immune complex diseases linked to increased incidence of HLA, are compounds of the following formula:

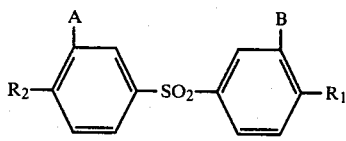 (I)

wherein:
A and B are hydrogen or fluoro, provided that A and B may not both be fluoro;
$R_1$ is loweralkanoylamino, loweralkoxycarbamoyl, nitro or ureido; and
$R_2$ is loweralkanoylamino, loweralkoxycarbonylamino, loweralkyl or nitro, and when $R_1$ is ureido, $R_2$ is additionally
(a) amino;
(b) a substituted amino moiety having the following structure:

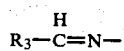 (II)

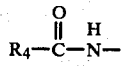 (III)

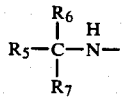 (IV)

wherein:
$R_3$ is (1) a phenyl group; optionally substituted with (i) chloro; (ii) hydroxy and loweralkoxy; (iii) hydroxy and chloro; (iv) hydroxy substituent(s); or (v) a 3,4-methylenedioxy substituent;
(2) a heterocycic 5-6 membered ring contain 1-2 hetero atoms selected independently from the group consisting of O, N, or S; or
(3) a branched alkyl group having 3-9 carbon atoms;
$R_4$ is (1) hydrogen; (2) amino; (3) cycloalkyl having 3-9 carbon atoms; (4) halomethyl, said halomethyl having a methyl group having one, two, or three halogens, said halogens being the same or different and being chloro, bromo, fluoro, or iodo; (5) haloethyl, said haloethyl having 1-5 halogen atoms, being the same or different; (6) loweralkenyl; (7) a heterocyclic 5-6 membered ring containing 1-2 hetero atoms independently selected from the group consisting of O or N; (8) a thioloweralkyl group having 1-6 carbon atoms; (9) an aminohydrocarbyl fragment as hereinafter defined; (10) a phenyl group having a carboxy, amino, or nitro substituent; or (11) 2-carboxyethyl;
$R_5$ is (1) hydrogen; (2) loweralkyl; (3) branched alkyl; or (4)-amino $R_3$;
(5) $NaSO_2—$; (6) $R_8SO_2—$;

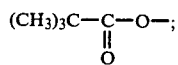 (7)

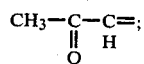 (8)

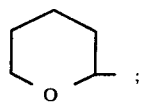 (9)

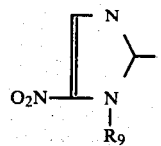 (10)

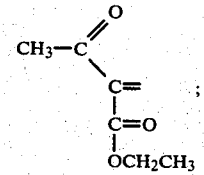 (11)

$HOCH_2(CHOH)_4—$ (12)

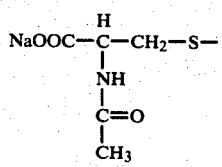 (13)

$R_6$ is hydrogen, the dotted line indicating that $R_6$ is not present when $R_5$ is attached to C with a double bond;
$R_7$ is (1) hydrogen; (2) loweralkyl; or (3) loweralkoxy;
$R_8$ is (1) phenyl having optional nitro, amino, methyl, or acetamido substituents; or (2) loweralkyl having 1-6 carbon atoms;
$R_9$ is (1) hydrogen; or (2) loweralkyl;

(c) 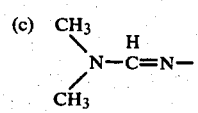 (V)

(d) 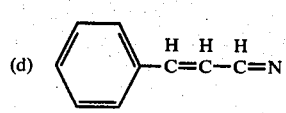 (VI)

(e) 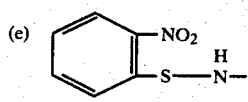 (VII)

(f) 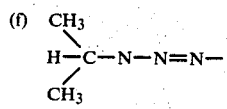 (VIII)

The compounds of Formula II (above) which are the sodium bisulfite and methanol adducts, i.e.,

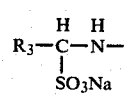

-continued
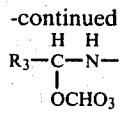

respectively, are also within the scope of the compounds useful in the pharmaceutical compositions and methods of treatment of the present invention.

By the term "aminohydrocarbyl fragment" is meant that $R_4$ is a portion of an amino acid. Thus, if

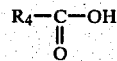

represents an amino acid, the following amino acids can be used to make compounds of Formula I: glycine, alanine, valine, leucine, isoleucine, phenylalanine, typosine, proline, hydroxyproline, serine, threonine, cysteine, cystine, methionine, tryptophane, aspartic acid, glutamic acid, argenine, lycine, or histidine. The corresponding portion of the amino acid is $R_4$ in the diphenyl sulfone of Formula I. For example, in the case of glycine:

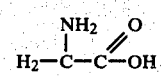

represents the amino acid, and $R_4$ is therefore

or aminomethyl.

Preferred compounds for use in the pharmaceutical compositions and methods of treatment of the present invention are those of formula:

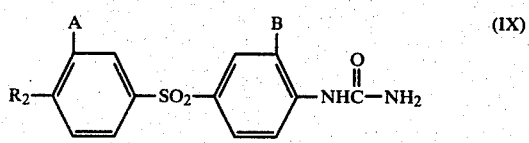

(IX)

wherein:
A and B are hydrogen or fluoro, provided that A and B may not both be fluoro;
$R_2$ is (a) amino;

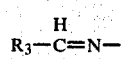
(b)

wherein $R_3$ is a phenyl group; optionally substituted with (i) chloro; (ii) hydroxy and loweralkoxy; (iii) hydroxy and chloro; (iv) hydroxy substituent(s); or (v) a 3,4-methylenedioxy substituent;

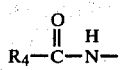
(c)

wherein $R_4$ is (1) hydrogen; (2) amino; (3) cycloalkyl having 3-6 carbon atoms; (4) halomethyl having one, two, or three halogens the same or different and being chloro, bromo, fluoro, or iodo; (5) a heterocyclic 5-6 membered ring containing 1-2 hetero atoms independently selected from the group consisting of O or N; and (6) an aminohydrocarbyl fragment; or

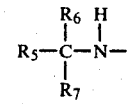
(d)

wherein $R_5$ is 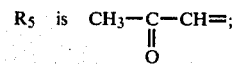

$R_6$ is not present; and
$R_7$ is loweralkyl.

The most preferred compounds for use in the pharmaceutical compositions and methods of treatment of the present invention are those of Formula IX wherein:
$R_2$ is (a) amino;

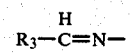
(b)

where $R_3$ is phenyl substituted with hydroxy and methoxy;

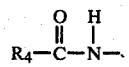
(c)

where $R_4$ is (1) hydrogen; (2) amino; (3) cyclohexyl; (4) trifluoromethyl; (5) furyl; and (6) the aminohydrocarbyl fragment of glycine, i.e., aminomethyl; or

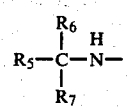
(d)

where $R_5$ is 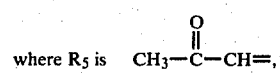

$R_6$ is not present, and $R_7$ is methyl.

The diphenyl sulfone compounds of Formula I for use in the pharmaceutical compositions and methods of treatment of the present invention are readily prepared by methods known in the art, for example, those described in U.S. Pat. Nos. 3,689,671; 3,702,362; 3,715,375; 3,775,403; 3,775,444; and 3,786,050.

For the purposes of treating rheumatoid arthritis, muscular dystrophy, and immune complex diseases linked to increased incidence of HLA, the compounds of Formula I may be administered orally, topically, parenterally, by inhalation spray or rectally in dosage unit formulations containing conventional nontoxic pharmaceutically acceptable carriers, adjuvants and vehicles. The term parenteral as used herein includes subcutaneous injections, intravenous, intramuscular, intrasternal injection, intraarticular, or infusion techniques. In addition to the treatment of warm-blooded animals such as mice, rats, horses, dogs, cats, guinea pigs, rabbits, etc., the compounds of the invention are effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide a pharmaceutically elegant and palatable preparation. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, maize starch, or alginic acid; binding agents, for example starch, gelatine or acacia, and lubricating agents, for example magnesium stearate, steric acid or talc. The tablets may be uncoated or they may be coated by known techniques to delay disintegration and adsorption in the gastrointestinal tract and thereby provide a sustained action over a longer period. For example, a time delay material such as glyceryl monosterate or glyceryl distearate may be employed.

Formulations for oral use may also be presented as hard gelatine capsules wherein the active ingredient is mixed with an inert solid diluent, for example, calcium carbonate, calcium phosphate or kaolin, or as soft gelatine capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, the example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and hexitol such as polyoxyethylene sorbitol monooleate, or condensation products of ethylene oxide with partial esters derived from fatty acids and hexitol anhydrides, for example polyoxyethylene sorbitan mono-oleate. The said aqueous suspensions may also contain one or more preservatives, for example ethyl, or n-propyl, p-hydroxy benzoate, one or more coloring agents, one or more flavoring agents, and one or more sweetening agents such as sucrose or saccharin.

Oily suspensions may be formulated by suspending the active ingredient in a vegetable oil, for example arachis oil, olive oil, sesame oil or coconut oil, or in a mineral oil such as liquid paraffin. The oil suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an antioxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the present invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally-occurring phosphatides, for example soya bean lecithin, and esters or partial esters derived from fatty acids and hexitol anhydrides, for example sorbitan mono-oleate, and condensation products of the said partial esters with ethylene oxide, for example polyoxyethylene sorbitan mono-oleate. The emulsions may also contain sweetening and flavoring agents.

Syrups and elixirs may be formulated with sweetening agents, for example glycerol, sorbitol or sucrose. Such formulations may also contain a demulcent, a preservative and flavoring and coloring agents. The pharmaceutical compositions may be in the form of a sterile injectable preparation, for example as a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono-or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

The compounds of Formula I may be administered as suspensions or solutions suitable for ophthalmic use, employing pharmaceutically acceptable carriers and excipients especially fit for the eye. The compounds of Formula I may also be administered to the eye by incorporation in a solid ophthalmic insert.

The daily dosage of the compounds of Formula I may be varied over a wide range from 1.0 to 2,000 mg. Preferably, the compound of Formula I, either by itself, or with a carrier in a pharmaceutical composition, is administered in subdivided doses containing 5, 10, 25, 50, 100, 150, 250 and 500 mg. of the active ingredient for the symptomatic adjustment of the dosage to the patient to be treated. An effective amount of the drug is ordinarily supplied at a dosage level of from about 0.01 mg. to about 50 mg./kg. of body weight. Preferably the range is from about 0.1 mg. to 7 mg./kg. of body weight.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

What is claimed is:

1. A method of treating rheumatoid arthritis comprising administering to a patient in need of such treatment a therapeutically effective amount of a compound of the formula:

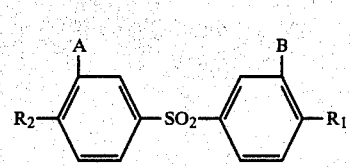

wherein:
A and B are hydrogen or fluoro, provided that A and B may not both be fluoro;
R$_1$ is loweralkanoylamino, loweralkoxycarbamoyl, nitro or ureido; and
R$_2$ is selected from the group consisting of loweralkanoylamino, loweralkoxycarbonylamino, loweralkyl and nitro, and when R$_1$ is ureido, R$_2$ is additionally selected from the group consisting of
(a) amino;
(b) a substituted amino moiety having the following structure:

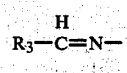

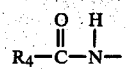

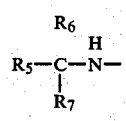

wherein:
R$_3$ is (1) a phenyl group; optionally substituted with (i) chloro; (ii) hydroxy and loweralkoxy; (iii) hydroxy and chloro; or (iv) hydroxy substituent; or (2) a branched alkyl group having 3-9 carbon atoms;
R$_4$ is (1) hydrogen; (2) amino; (3) cycloalkyl having 3-9 carbon atoms; (4) halomethyl, said halomethyl having a methyl group having one, two, or three halogens, said halogens being the same or different and being chloro, bromo, fluoro, or iodo; (5) haloethyl, said haloethyl having 1-5 halogen atoms, being the same or different; (6) loweralkenyl; (7) a thioloweralkyl group having 1-6 carbon atoms; (8) an aminohydrocarbyl fragment; (9) a phenyl group having a carboxy, amino, or nitro substituent; or (10) 2-carboxyethyl;
R$_5$ is selected from the group consisting of (1) hydrogen; (2) loweralkyl; (3) branched alkyl; (4) -amino R$_3$; (5) NaSO$_2$—; (6) R$_8$SO$_2$—;

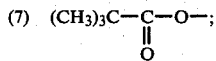

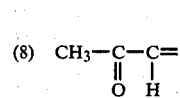
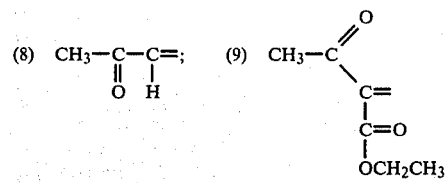

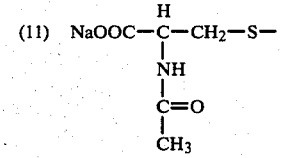

R$_6$ is hydrogen, the dotted line indicating that R$_6$ is not present when R$_5$ is attached to C with a double bond;
R$_7$ is (1) hydrogen; (2) loweralkyl; or (3) loweralkoxy;
R$_8$ is (1) phenyl having optional nitro, amino, methyl, or acetamido substituents; or (2) loweralkyl having 1-6 carbon atoms;

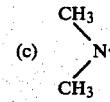
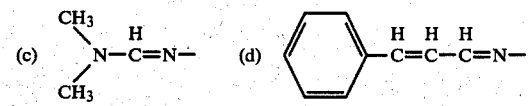

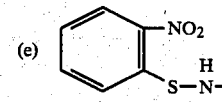
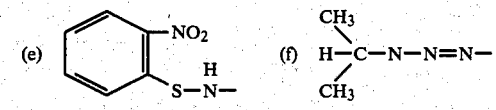

2. A method of treating rheumatoid arthritis, comprising administering to a patient in need of such treatment a therapeutically effective amount of a compound of the formula:

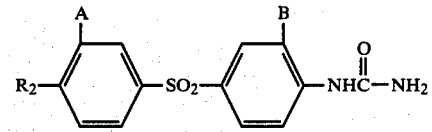

wherein:
A and B are hydrogen or fluoro, provided that A and B may not both be fluoro; and
R$_2$ is selected from the group consisting of
(a) amino (b)
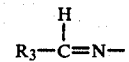

wherein R$_3$ is a phenyl group; optionally substituted with (i) chloro; (ii) hydroxy and loweralkoxy; (iii) hydroxy and chloro; or (iv) hydroxy substituent;

(c)
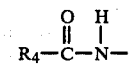

wherein R$_4$ is (1) hydrogen; (2) amino; (3) cycloalkyl having 3-6 carbon atoms; (4) halomethyl having one, two, or three halogens the same or different and being chloro, bromo, fluoro, or iodo; or (5) an amino-hydrocarbyl fragment; and

 (d)

wherein

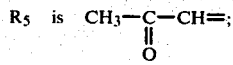

$R_6$ is not present; and $R_7$ is loweralkyl.

3. A method of treating rheumatoid arthritis comprising administering to a patient in need of such treatment a therapeutically effective amount of a compound of the formula:

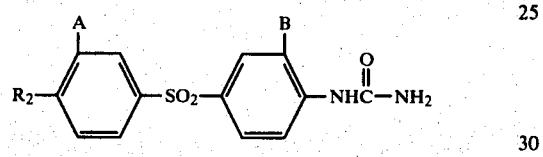

wherein:

A and B are hydrogen or fluoro, provided that A and B may not both be fluoro; and $R_2$ is selected from the group consisting of (a) amino;

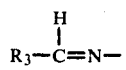 (b)

where $R_3$ is phenyl substituted with hydroxy and methoxy;

 (c)

where $R_4$ is (1) hydrogen; (2) amino; (3) cyclohexyl; or (4) trifluoromethyl; and

 (d)

where $R_5$ is 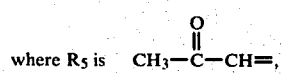

$R_6$ is not present, and $R_7$ is methyl.

4. The method according to claim 1 wherein
$R^1$ is ureido;
$R^2$ is HCONH— or amino;
A is fluoro; and
B is hydrogen 5. The method of claim 1 wherein
$R_1$ is ureido;
$R_2$ is HCONH— or amino;
A is hydrogen; and
B is fluoro or hydrogen.

6. The method of claim 1 wherein the compound is 1-[4-(4-sulfanilyl)phenyl]urea.

* * * * *